United States Patent
Thomas

(10) Patent No.: US 7,527,940 B2
(45) Date of Patent: May 5, 2009

(54) METHOD FOR THE DETERMINATION OF CHANGES IN A CELLULAR MORPHOLOGICAL PARAMETER

(75) Inventor: Nicholas Thomas, Cardiff (GB)

(73) Assignee: GE Healthcare UK Limited, Amersham (GB)

( * ) Notice: Subject to any disclaimer, the term of this patent is extended or adjusted under 35 U.S.C. 154(b) by 325 days.

(21) Appl. No.: 10/514,924

(22) PCT Filed: May 7, 2003

(86) PCT No.: PCT/GB03/01904

§ 371 (c)(1),
(2), (4) Date: Nov. 12, 2004

(87) PCT Pub. No.: WO03/098210

PCT Pub. Date: Nov. 27, 2003

(65) Prior Publication Data

US 2005/0227310 A1    Oct. 13, 2005

(30) Foreign Application Priority Data

May 15, 2002   (GB) ................. 0211072.4

(51) Int. Cl.
*C12Q 1/02* (2006.01)
(52) U.S. Cl. .................. 435/29; 435/34; 435/968
(58) Field of Classification Search .............. None
See application file for complete search history.

(56) References Cited

U.S. PATENT DOCUMENTS

| | | | |
|---|---|---|---|
| 5,635,608 A * | 6/1997 | Haugland et al. | 536/1.11 |
| 5,885,840 A * | 3/1999 | Kamentsky et al. | 436/63 |
| 6,416,959 B1 * | 7/2002 | Giuliano et al. | 435/7.2 |
| 6,902,883 B2 * | 6/2005 | Dunlay et al. | 435/4 |
| 6,933,154 B2 * | 8/2005 | Schomacker et al. | 436/164 |
| 6,986,993 B1 * | 1/2006 | Ghosh et al. | 435/7.1 |
| 7,060,445 B1 * | 6/2006 | Dunlay et al. | 435/7.1 |
| 2004/0253726 A1 * | 12/2004 | Gawad | 435/446 |

FOREIGN PATENT DOCUMENTS

WO    WO 99/47963    * 9/1999

OTHER PUBLICATIONS

Rapp S. et al. Microtubule Based Peroxisome Movement. J of Cell Science vol. 109, pp. 837-849, 1996.*
Peyser L. et al. Photoactivated Fluorescence from Individual Silver Nanoclusters. Science 291 (5501)103-106, Jan. 5, 2001.*
Adams S. et al. Controlling Cell Chemistry with Caged Compounds. Annu Rev Physiol 1993 vol. 55, 755-784.*
Smith, C., "Cytoskeletal Movements and Substrate Interactions during Initiation of Neurite Outgrowth by Sympathetic Neurons in vitro", *The Journal of Neuroscience*, vol. 14, No. 1, Jan. 1994, p. 384-398.*
Rapp, S., et al., "Microtubule-based peroxisome movement", *Journal of Cell Science*, vol. 109, 1996, p. 837-849.*
Oyesiku, N., et al., "Ciliary Neurotrophic Factor Stimulates Neurite Outgrowth From Spinal Cord Neurons", *The Journal of Comparative Neurology*, vol. 364, 1996, p. 68-77.*
Cooper, M., et al, "Confocal Microscopic Analysis of Morphogenetic Movements", *Methods in Cell Biology*, vol. 59, 1999, p. 179-204.*
Dailey, M., et al., "Cell Motility and Cell-Cell Interactions of Activated Microglia in Live Brain Slice Cultures", *Society for Neuroscience Abstracts*, vol. 27, 2001, p. 1323.*

* cited by examiner

*Primary Examiner*—Ralph Gitomer
(74) *Attorney, Agent, or Firm*—Yonggang Ji

(57) ABSTRACT

Disclosed is method for measuring a change in a cellular morphological parameter, for example, the position and/or the shape of a cell. The method comprises labelling a population of cells with a marker substance which is in a non-detectable state, but which may be caused to become detectable by exposure to light of a suitable first wavelength. By exposing a sub-population of labelled cells to light of an appropriate first wavelength in a predetermined pattern, the sub-population of cells may be defined in which the area covered by the sub-population conforms to the pattern of illumination used. Subsequent examination of at least a portion of the population of cells using illuminating light of a second wavelength selected to be suitable for detection of the marker, will reveal patterns of distribution of the marker substance indicative of a change in said cellular morphological parameter. Also described and claimed is a method for screening for a test agent whose effect on the cellular morphological parameter is to be determined.

8 Claims, 6 Drawing Sheets

METHOD FOR THE DETERMINATION OF CHANGES IN A CELLULAR MORPHOLOGICAL PARAMETER

CROSS REFERENCE TO RELATED APPLICATIONS

This application is a filing under 35 U.S.C. § 371 and claims priority to international patent application number PCT/GB03/01904 filed May 7, 2003, published on Nov. 27, 2003 as WO 03/098210 and also claims priority to patent application number 0211072.4 filed in Great Britain on May 15, 2002; the disclosures of which are incorporated herein by reference in their entireties.

BACKGROUND OF THE INVENTION

1. Field of the Invention

The present invention relates to a novel method for measuring a change in a cellular morphological parameter, for example the position and/or the shape of a cell, the method having improved throughput and being compatible with automation.

2. Description of Related Art

Cell motility is an essential element in a variety of normal and aberrant cellular processes. Many cell types exhibit dramatic changes in their morphology, such as movement, elongation of nerve axons and changes in shape during cell division. Wound healing, embryogenesis and immune system responses such as chemotaxis all require specialised cell types to recognise and respond to external stimuli by undergoing cell movement. Investigation of the mechanisms controlling cell movement and development of agents which can modulate cell movement are of significant interest in the development of new therapeutics. Measurement of neurite outgrowth and the effects of candidate drugs on this process are key to evaluating potential treatments for variety of injuries including stroke and spinal cord damage, and for neurodegenerative conditions such as Parkinson's and Alzheimer's diseases.

A variety of methods have been described for the measurement of cell movement. They fall into two general categories. The first of these relates to methods in which cells are positioned on one side of a membrane barrier and movement of the cells through the barrier is measured (Hagedorn et al, Biochim. Biophys. Acta, (1995), 1269(3), 221-232; Bock and Mrowietz, J. Biochem. Biophys. Methods, (2001), 48(3), 257-268); Dunzendorfer et al, Immunol. Lett., (2000), 71(1), 5-11). The second utilises optical methods for measuring cell movement, which methods typically involve acquiring a series of time lapse images of cells and then performing analysis of the images to measure cell movement (Thurston et al, Cytometry, (1988), 9, 411-417; Thurston et al, Experimental Cell Research, (1986), 165, 380-390).

Major efforts in central nervous system research are focused on the identification of compounds that affect the growth of neurites. Agents that promote nerve growth have therapeutic potential in a wide variety of diseases and traumas, including stroke, spinal cord injuries, and neurodegenerative conditions such as Parkinson's and Alzheimer's diseases. Current methods for measuring neurite outgrowth rely on manual examination of individual cells, or use of complex image analysis methods, to determine the extent of neurite outgrowth from cell bodies (Jiang, Z. G. et al, Brain Res. Dev. Brain Res., (1995), 85(2), 212-9; Patrick, C. W. et al, Exp. Neurol., (1996), 138(2), 277-85). Methods for measuring neurite outgrowth are described in WO 01/11340 by the use of neuronal cells containing a luminescently labeled reporter molecule that reports on cell location, and a second luminescently labeled reporter molecule that reports on neurite outgrowth. Changes in the distribution, environment or activity of the first and second luminescently labelled reporter on or within the cells is determined by digital imaging. This method, while an improvement over image analysis methods based purely on morphology analysis, still requires complex analysis procedures to determine the relative spatial arrangement of the two luminescent reporters.

To date, the methods to measure cellular movement are generally labour intensive to set up, and while variants have been devised using disposable components and chemical analysis methods to determine the number of cells crossing barrier membranes (Frevert et al, J. Immunol. Methods, (1998), 213(1), 41-52), they remain unsuitable to high-throughput applications. Imaging methods have the disadvantage that the analysis process can be extremely complex as sufficient images must be accumulated to enable tracking of individual cells from one image to the next in a series. In addition, since mammalian cells in culture can achieve quite significant relative rates of movement of up to 1-2 µm/minute, (Zicha et al, J. Cell Sci., (1999), 112, 447-454; Thurston and Palcic, Cell Motility and the Cytoskeleton, (1987), 7, 361-367), a single cell of size 10-20 µm can readily move to a position which is non-coincident with its former position in 10-30 minutes. Since cell migration measurements may be performed over many hours or longer, time lapse film or video recording must collect sufficient information to track all cells to avoid misidentification of cells between images. Additionally, once images have been obtained, intensive manual analysis or sophisticated software is required to analyse data and determine the translocation of each cell in a population (Thurston et al, (1988), loc cit; Thurston et al, (1986), loc cit).

Some attempts have been made to simplify assays to make them more suitable for automation in high throughput. These assays have used fluorescent intensity measurements of labelled cells either in standard culture, or in cultures on membrane barriers (Crouch M. F., J. Neurosci. Methods, (2000), 104(1), 87-91), where neurite growth from fluorescently-labelled cells through a membrane is measured. These assays permit quantitation of neurite outgrowth to be performed using fluorescence intensity measurements alone. However, intensity measurements performed on standard cultures cannot accurately discriminate between fluorescently labeled neuronal cell bodies and neurites, leading to inaccuracy in measurement of neurite outgrowth. Barrier methods, while permitting discrimination between cell bodies and neurites, suffer from the same problems in setting up assays as previously described for barrier cell migration methods.

SUMMARY OF THE INVENTION

The preceding methods are characterised by the use of physical barriers and/or individual cell identification to determine changes in cellular morphology. Consequently, they impose high requirements for manual intervention and/or analytical effort, allied to sophisticated instrumentation and software that preclude large numbers of analyses being performed in parallel. There is a need, therefore, for methods of measuring cellular morphological changes that require minimal set up procedures and are compatible with high-throughput screening and automation. The present invention provides a method of measuring a change in a morphological property of a cell, particularly a change in cell position and/or cell shape, which avoids the requirements for physical barriers to segregate cell populations and furthermore avoids the need to track individual cells. Methods are thereby provided for cell analysis that can be used with a wide range of cell types and culture conditions, the results of which can be analysed using available instrumentation.

Accordingly, in a first aspect of the invention, there is provided a method of measuring a change in a cellular morphological parameter the method comprising:
a) exposing a sub-population of cells in a cell population to light of a first wavelength wherein said cell population is labelled with a marker substance that is capable of being converted from a substantially non-detectable state into a detectable state by exposure of the marker to light of a first wavelength;
b) at a first time exposing at least a portion of said cell population to light of a second wavelength and detecting a first pattern of distribution of said marker substance; and
c) at a second time exposing said portion of said cell population to light of the second wavelength and detecting a second pattern of distribution of said marker substance;
wherein a difference between said first and second patterns of distribution of said marker substance is indicative of a change in said cellular morphological parameter.

Preferably, the cellular morphological parameter is selected to be cell size, cell position and/or cell shape and a change in the pattern of distribution of said marker substance in said sub-population is indicative of a change in cell size and/or position and/or the shape of the cell. In a particularly preferred embodiment, the change in cell shape is indicative of neurite outgrowth.

Thus, according to the method of the present invention, measurement of a cellular morphological parameter is achieved by labelling a population of cells with a marker substance which is in a non-detectable state, but which may be caused to become detectable by exposure to light of a suitable first wavelength. By exposing a sub-population of labelled cells to light of an appropriate first wavelength in a predetermined pattern, the sub-population of cells may be defined in which the area covered by the sub-population conforms to the pattern of illumination used. Subsequent examination of at least a portion of the population of cells using illuminating light of a second wavelength, selected to be suitable for detection of the marker, will reveal only those cells in which the marker was exposed to light of the first wavelength.

The portion of the cell population that is examined with light of the second wavelength according to steps b) and c), may be:
i) the whole cell population, wherein all cells are exposed to light of the second wavelength, and the pattern of distribution of the marker substance is recorded across all cells, such examination being achieved by removing the means of light patterning used to achieve illumination with light of the first wavelength; or,
ii) a sub-population of cells, wherein the same sub-population of cells that is exposed to light of the first wavelength is exposed to light of the second wavelength, and the pattern of distribution of the marker substance is recorded, such examination being achieved by retaining the spatial position of the means of light patterning used to achieve illumination with light of the first wavelength, and using this means to effect illumination with light of the second wavelength; or,
iii) a sub-population of cells, wherein a different sub-population of cells to that exposed to light of the first wavelength is exposed to light of the second wavelength, and the pattern of distribution of the marker substance is recorded, such examination being achieved by altering the spatial position of the means of light patterning used to achieve illumination with light of the first wavelength, and using this means to effect illumination with light of the second wavelength.

The method according to the invention may be used with any adherent cell type that can be cultured by standard tissue culture methods. Such cell types include all normal and transformed cells derived from any recognised source with respect to species (e.g. human, rodent, simian), tissue source (e.g. brain, liver, lung, heart, kidney skin, muscle) and cell type (e.g. epithelial, endothelial). In addition, cells which have been transfected with recombinant genes may also be cultured and utilised in the method of the invention. There are established protocols available for the culture of diverse cell types. (See for example, Freshney, R. I., Culture of Animal Cells: A Manual of Basic Technique, $2^{nd}$ Edition, Alan R. Liss Inc. 1987). Such protocols may require the use of specialised coatings and selective media to enable cell growth and the expression of specialist cellular cell morphological parameters.

Suitably, the changes in a morphological parameter of living cells may be categorised as:
i) transient morphological changes in which cells exhibit a change in size, shape or position, while at least part of the cell occupies the same space, for example, when cells in culture grow and divide;
ii) changes in cell position involving the movement of cells in a random manner (cell motility), or movement of cells towards or away from a chemical or physical stimulus (cell migration), in which the cell position changes such that the entire cell occupies a space which is non-overlapping with a previously occupied position; and
iii) permanent morphological changes of the cell size and shape, typically occurring as a result of cell differentiation and which may result in a significant increase in cell mass and area.

While all cultured cells will show morphological changes according to category i), certain specialised biological processes may involve one or both of categories ii) and iii). For example, fibroblasts stimulated with cytokines show directed chemotaxis (Sasaki, et al, Mediators Inflamm., (2000), 9(3-4), 155-60) orientated to a chemo-attractant gradient. In this case, cell behaviour corresponds to category ii) above. In PC12 cells, NGF induced differentiation causes cells to lose motility and produce outgrowths of neurites (Green and Reid, Nature, (1977), 268, 349), a neurite being classified as a cell outgrowth of length greater than twice the diameter of the cell body. In this case, cell behaviour corresponds with category iii). In myotube formation, the process whereby individual muscle cells form muscle fibres, individual cells migrate preferentially towards areas with high densities of cells and subsequently fuse with other cells to form linear fibres (Chazaud et al, J. Muscle Res. Cell Motil., (1998), 19(8), 931-6). In this case, cells exhibit both category ii) and iii) behaviour.

In one embodiment according to the first aspect, the present invention provides a method of measuring changes in a cellular morphological parameter over time, by further examination of the sub-population of marked cells at least once. Such changes may result from the expansion and/or diffusion over time of the pattern of the detectable marker. This may be accomplished without the need to identify or track individual cells. In this embodiment, the method comprises following step c): exposing said portion of said cell population to light of said second wavelength N further times where N is $\geq 1$, and detecting a pattern of distribution of said marker substance wherein the patterns of distribution of said marker substance are used to create a profile indicative of changes in said cellular morphological parameter.

In a particular embodiment according to the first aspect, there is provided a method for screening for a test agent whose effect on the cellular morphological parameter is to be determined. The method comprises the steps of: (a) performing the method according to the first aspect in the presence and in the absence of said agent; and (b) measuring a difference between the patterns of distribution of said marker substance in the presence and in the absence of said agent; wherein a difference between the patterns of distribution in the presence and in the absence of said test agent is indicative of the effect of said agent on the cellular morphological parameter. Alternatively, the measuring can be done by performing the method in the presence of a test agent and comparing the pattern of distribution of the marker substance with a control pattern of distribution measured in the absence of the test agent. The control pattern may conveniently be stored electronically in a database or other electronic format.

Suitably, the marker substance for labelling cells according to the invention is a marker that may be converted from a non-detectable or substantially non-detectable state into a detectable state, by exposure of the marker to light of a suitable wavelength. Suitable marker substances may be separated into two categories according to their properties and method of use.

In the first category, markers, herein defined as direct markers, are acted on directly by light to convert the marker into a detectable state. Direct markers may be loaded into, or attached to, all cells in a population and a sub-population of cells subsequently marked by exposure to light of defined geometry. Suitable substances for use as direct markers include caged fluorescent molecules, photochromic molecules and photochromic proteins. Direct markers may also contain a second moiety, capable of influencing the biophysical or fluorescence properties of the reporter molecule. In such cases, the reporter is non-fluorescent in the extracellular media and fluorescent within, or when attached to the cell, following exposure to light. Suitable substances for use as direct markers in this category include; enzyme substrate-photochromic fluorescent dyes, membrane sensitive-photochromic dyes and pH sensitive-photochromic dyes.

Markers according to the second category, herein defined as indirect markers, do not alter their detection properties when exposed to light, but may be used in conjunction with other photoactivatable substances. Indirect markers may be loaded into, or attached to, a sub-population of cells within a total population by exposure to light of defined geometry. Suitable substances for use as indirect markers include self-quenching fluors contained at high concentration within photoactivatable liposomes and photoreactive labels.

Preferred marker substances for use according to the invention have a number of desirable properties, as are described below:
a) they should be freely soluble in aqueous media and buffers;
b) they should be freely permeable across or into cell membranes, but retained inside or in association with cells; and
c) they should be non-detectable or substantially non-detectable in free solution and inside cells in the absence of light of a wavelength suitable for activation.

Particularly preferred marker substances for use according to the invention have a number of additional properties:
a) non-detectable or substantially non-detectable in free solution following exposure to light of a wavelength suitable for activation; and
b) detectable inside cells following exposure to light of a wavelength suitable for activation.

Reporter molecules having these characteristics are desirable to permit a population of cells to be exposed to solution of a non-detectable or substantially non-detectable marker substance, to permit all cells to become loaded with the marker, and to permit conversion to a detectable marker within a sub-population of cells, without conversion of the bulk marker in free solution causing interference with analysis.

A caged fluorescent molecule is a molecule whose fluorescence properties may be controlled by photolytic conversion from an inactive (non-fluorescent) form to an active (fluorescent) form. A variety of caging groups are available and several of these have been used to generate caged fluorophores which are non fluorescent until "un-caged" by illumination with UV light (Adams and Tsien, Ann. Rev. Physiol., (1993), 55, 755-784; Handbook of Fluorescent Probes and Research Products, (2001), Molecular Probes).

Suitable examples of caged fluorescent molecules for use in the method according to the present invention include N-(DMNB-caged fluorescein)-1,2-dihexadecanoyl-sn-glycero-3-phosphoethanolamine and 5-carboxyfluorescein-bis-(5-carboxymethoxy-2-nitrobenzyl)ether-alanine-carboxamide, succinimidyl ester (Molecular Probes Inc.). These caged fluors may be "un-caged" by brief exposure to UV light of wavelength 300-360 nm. In principle any caged fluorescent molecule which can be attached to, or incorporated into, living cells can be used in the method of the invention.

In the alternative, the marker may be a photochromic material which exhibits switchable fluorescence. Suitable photochromic materials include silver oxide nanocluster particles (Peyser, et al, Science, (2001), 291 103-106) which are activated by illumination with 488 nm light such that subsequent illumination by light at 520-550 nm causes the particles to fluoresce, while particles not previously exposed to 488 nm illumination do not fluoresce when excited at 520-550 nm. Other fluorescence based photochromic switches are described, for example fulgide derivatives (Inada, T., et al, Chem. Lett., (1997), 321; Inada, T., et al, Chem. Lett., (1997), 961; Walz, J., et al, Chem. Phys. Lett., (1993), 213, 321-324; and dihydroazulene derivatives (Daub, J., et al, Mol. Cryst. Liq. Cryst., (1992), 217, 177-185).

Alternative photochromic materials for use in the method according to the present invention include photochromic molecules such as spirobenzopyrans and naphthacenequinones as described in U.S. Pat. Nos. 5,268,862 and 5,847,141. Such materials change colour when irradiated with UV, visible or infrared radiation while in a ground state. The molecule then undergoes a photochemical conversion to a metastable state, where the metastable state absorbs light at a different wavelength to the ground state.

Photochromic proteins are fluorescent proteins having two or more stable states with differing excitation or emission spectra in which the photochromic proteins are switched between states by irradiation with light of an appropriate wavelength. U.S. Pat. No. 6,046,925 describes optical memory devices comprising photochromic fluorescent proteins. In one embodiment, the photochromic protein is a variant of Aequorea green fluorescent protein (GFP) which includes an amino acid substitution of T203, such as T203F, T203Y, T203S, S65G/S72A/T203F, S65G/S72A/T203Y, or T203S/S205T. A further GFP variant has been described (Patterson, G. H. and Lippincott-Schwartz, J., Science, (2002), 297, 1873-7) that, after intense irradiation with 413 nanometer light, increases fluorescence 100 times when excited by 488 nanometer light, and remains stable for days under aerobic conditions. Expression of GFP is widely used as a fluorescent probe and marker in living cells (Misteli, T.

and Spector, D. L., Nat. Biotechnol., (1997), 15(10), 961-4). Photochromic variants of GFP or other photochromic fluorescent proteins engineered for constituitive expression in living cells using methods which are well known to those skilled in the art (see, for example, the techniques described in Maniatis, et al., Molecular Cloning, A Laboratory Manual, Cold Spring Harbor Laboratory, N.Y., (1989)) provide further means of marking cells by the method of the present invention.

Other examples of direct markers that may be used in conjunction with photochromic materials include materials that are non-fluorescent until they have reacted with intracellular components, for example Bimane derivatives, for example monobromobimane. Upon passive diffusion into the cell and reaction with intracellular glutathione- and thiol-containing proteins, blue fluorescent adducts are formed.

Labelling of cells using the marker substance according to the present invention may be achieved by use of a methodology appropriate to the design of the marker substance. For example, methods are available for labelling the cytoplasm of the cell under study, or, alternatively the marker may be used to label the cell surface. The choice of labelling method is dependent on the type of marker substance that is employed and will be apparent to the skilled person. For example, cell surface labelling will permit the use of photochromic materials in the method of the present invention. Alternatively, the marker substance may be loaded into cells by micro-injection or by established bulk loading methods, for example Influx™, supplied by Molecular Probes.

A further method of providing activation of a non-detectable marker to a detectable form suitable for use in the current invention is to compartmentalise the label in a form in which it is not detectable. Rendering a fluorescent molecule non-detectable may be achieved, for example, by segregating a fluorescent moiety in a vesicle in which the high concentration of the label causes loss of fluorescence by self quenching, or by encapsulating an pH-sensitive fluorescent moiety in an environment of a pH at which it is non-fluorescent. Introduction of the encapsulated fluorescent moiety and subsequent release by exposure to patterned illumination permits spatially controlled conversion of the fluorescent molecule from a non-detectable form to a detectable form. Light activated release of compounds from photosensitive liposomes into living cells by UV photolysis has been described for drug delivery applications (Bisby, R. H. et al, Photochem. Photobiol., (2000), 72(1), 57-61; Morgan, C. G. et al, Photochem. Photobiol., (1995), 62(1), 24-9). Encapsulation of a suitable fluorescent label into liposomes containing a photochromic lipid such as (1,2-(4'-n-butylphenyl)azo-4'-(gamma-phenyl-butyroyl))-glycero-3-phosphocholine (Morgan C. G., et al, Biochim. Biophys. Acta, (1987), 903(3), 504-9), which isomerizes on exposure to near-UV light with resulting changes in membrane permeability to solutes, and consequent light directed fusion with cell membranes provides a means of delivery of a fluorescent label to cells to permit marking cells according to the present invention.

Suitable fluorescent molecules for use in this method of labelling include those such as fluorescein which are non-fluorescent due to self quenching when compartmentalised at high local concentrations (Shi, L. B. and Verkman, A. S., J. Gen. Physiol., (1989), 94(6), 1101-15), but become fluorescent when diluted, for example, when released into a cell by light directed fusion of a liposome with the cell membrane. Alternatively, fluorescent molecules such as 2',7'-bis-(2-carboxyethyl)-5-(and-6)-carboxyfluorescein (Molecular Probes) which are pH sensitive, may be used. For example, a pH sensitive fluor may be encapsulated in photosensitive liposomes in a solution of acid pH, under which conditions the molecules exhibit low fluorescence, but when released into a cell by photolysis of the liposome and exposed to a higher pH the molecules increase in fluorescence. Additional pH sensitive fluorescent molecules for use in the invention are the pH sensitive cyanine dyes as described in WO 00/75237.

A further group of labels suitable for use in the method of the present invention are photoreactive or photoaffinity labels which comprise a fluor or other detectable moiety linked to a reactive group which is activated by exposure to light of an appropriate wavelengths and which consequently forms a covalent bond with an adjacent moiety. Examples of photoreactive labels include ethidium monoazide (Molecular Probes), aryl azides (Bronk, K. S. and Walt, D. R., Anal. Chem., (1994), 66(20), 3519-20), azido-rhodamine (Daoud, R. et al, Biochemistry, (2000), 39(50), 15344-52) and carbocyanine nitrophenylazide (Hahn, K. M. et al, J. Histochem. Cytochem., (1993), 41(4), 631-4). Use of such labels in the method of the invention may be achieved by exposure of cells to the photoreactive molecule in the presence of patterned illumination of an appropriate wavelength to cause activation and labelling, followed by removal of uncoupled photoreactive molecules by washing, to yield a pattern of labelled cells.

BRIEF DESCRIPTION OF THE DRAWINGS

In order to clarify the principle and the function of the invention, reference is now made to the accompanying drawings and figures in which.

DETAILED DESCRIPTION OF THE INVENTION

Figure 1:
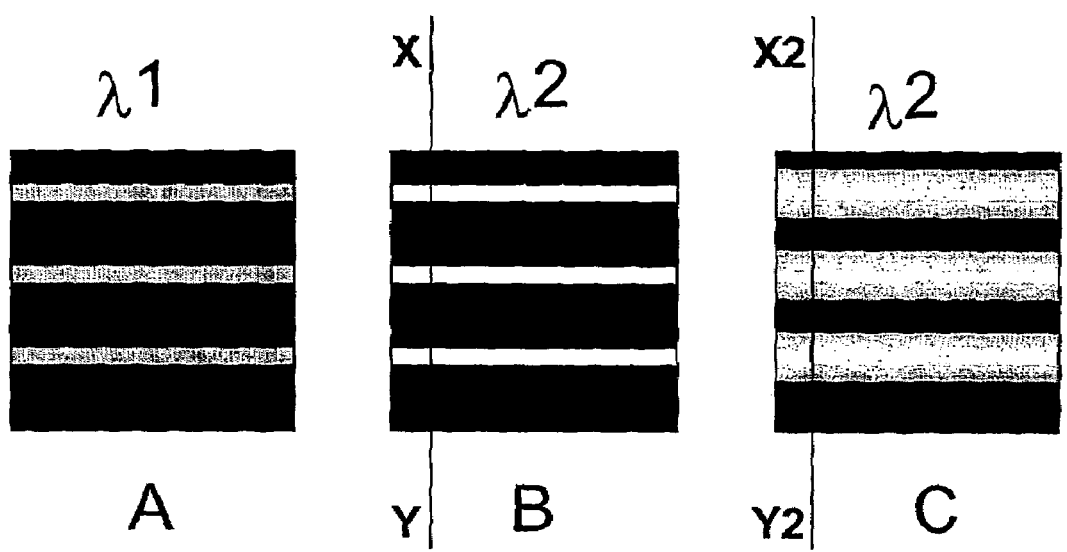
FIG. 1 is a schematic diagram of light activated patterning of cells and subsequent analysis of cell distribution.
Figure 2:
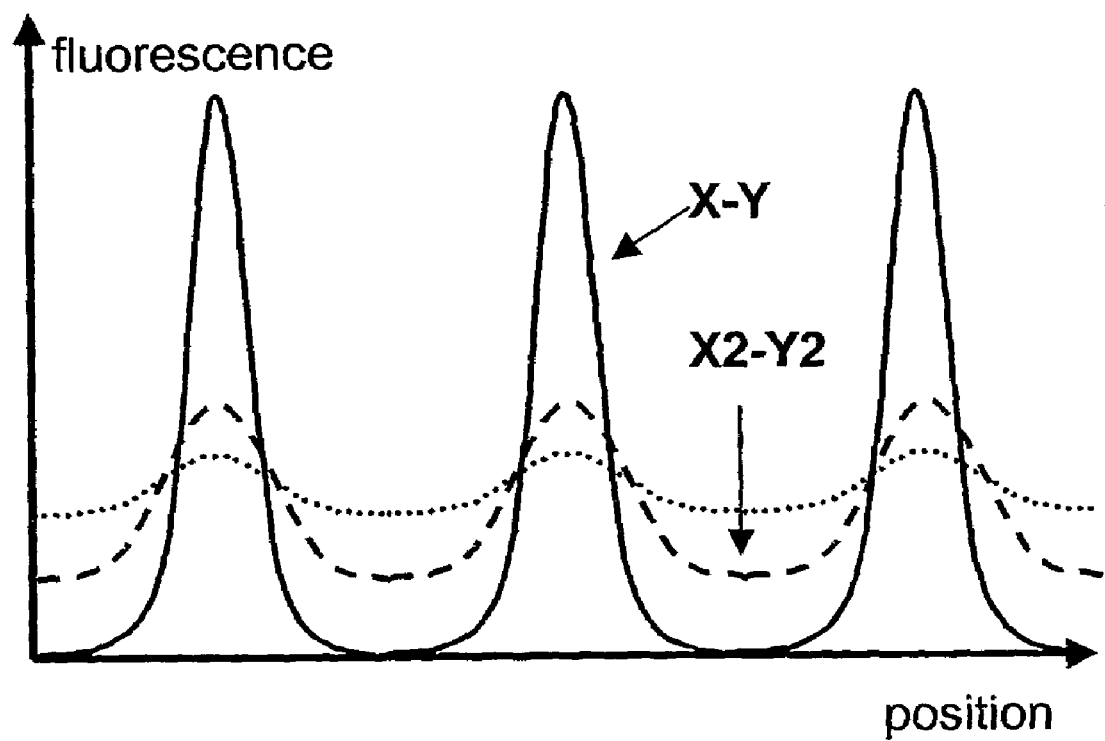
FIG. 2 is a diagram showing the analysis of cell distribution following cell migration.

The following aspect of the present invention is described with reference to FIGS. 1 and 2. Cells growing on a surface (represented by the black square of FIG. 1A) are labelled with a non-detectable marker substance. A sub-population of cells is subsequently illuminated by light of a first wavelength, hereinafter termed $\lambda 1$, where $\lambda 1$ is selected to be a suitable wavelength for activation of the label by causing conversion of the label from a non-detectable state to a detectable state and where the cell sub-population is in a defined pattern bounded by the area of illumination (represented by the grey bars in FIG. 1A). Subsequent illumination of the same area of cells (represented by the black square in FIG. 1B) with light of wavelength $\lambda 2$, where $\lambda 2$ is of longer wavelength than $\lambda 1$, reveals the pattern of the detectable label (white bars in FIG. 1B) caused by the patterned illumination at $\lambda 1$. Subsequently, the cells may be re-examined at one or more or more predetermined time intervals by illumination of the same area of cells (represented by the black square in FIG. 1C) with light of wavelength $\lambda 2$. This will result in a different pattern of detectable label (as represented by the broader shaded bars in FIG. 1C), if a change in a cell position has occurred. Thus, cells initially exposed to light of wavelength $\lambda 1$ are shown to have moved from their original position, as evidenced by a diffused or otherwise altered pattern of detectable label, compared with the pattern created by the initial illumination of the sub-population of cells using light at wavelength λ1. The wavelength of the illuminating light, λ2, is selected so as to be suitable for detection of the marker substance and will reveal only those cells in which the marker substance was exposed to light of the first wavelength λ1.

The degree of change in cell movement and/or cell shape can be readily determined by comparing the distribution pattern of cells carrying the detectable label by comparing an appropriate characteristic of the distribution of label. For example, as illustrated in FIG. 2, determining the distribution of label along a line transecting the illuminated pattern (represented by line X-Y of FIG. 1B) at the beginning of a cell migration assay and repeating this measurement at a later time (represented by line X2-Y2 of FIG. 1C) will result in a clear difference in pattern profiles as shown in FIG. 2, where cell movement results in diffusion and broadening of the intensity profile of the illuminated pattern.

In principle, any pattern or number of pattern elements may be used for the illumination step using light of wavelength λ1. Spots, lines or other geometric shapes may be achieved by continuous or intermittent lateral motion of an illumination point in one or two dimensions. Patterning of illumination may be achieved by scanning a focussed point of illumination across a surface, either by moving the illumination point relative to the specimen or vice versa, or by a combination of movements.

Figure 3:
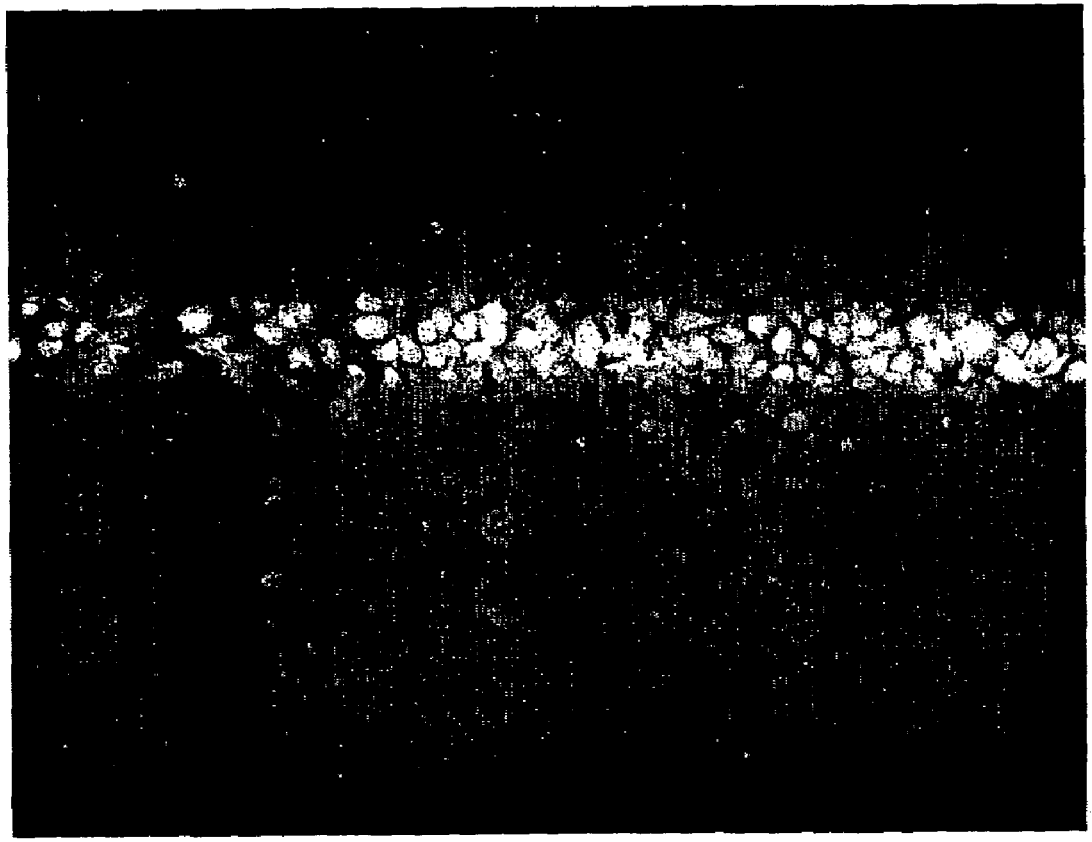
FIG. 3 is an electronic image showing HeLa cells labelled with a caged fluorescent label and patterned using UV light.

Scanning confocal microscopes, for example the Zeiss LSM400, scan a small focussed point of light across the specimen. By controlling the motion of the illumination point, or by restricting the motion of the illumination point and moving the specimen stage, the illumination point can be caused to illuminate a defined pattern. Alternatively non-scanning fluorescence microscopes, for example the Nikon Diaphot, which use a fixed illumination source may be used to produce a pattern of illumination on a specimen by using a combination of a high magnification objective and a partially closed illumination iris to project a small spot of light onto the specimen. Movement of the specimen stage in one or two dimensions can then be used to create virtually any desired pattern of illumination. Activation of a caged fluorochrome label in HeLa cells by this method is illustrated in FIG. 3.

In each of the examples according to the invention, multiple or repeating pattern elements may be achieved by blocking or switching off the illumination light while the specimen and/or the point of illumination is moved, to allow the illumination of non-contiguous areas.

Other forms of scanning microscopy instrumentation, for example, the Amersham Biosciences IN Cell Analysis System, illuminate the specimen with a line of light of a defined wavelength. Such line scanning systems may be used in the method of the invention to produce a pattern of parallel lines on a specimen by scanning an intermittently modulated line of light across the specimen.

Alternatively, a predetermined pattern of illumination may be achieved by illumination of the specimen with light passed through a partially opaque patterned mask such that the mask pattern is focussed on the specimen. Such masks are commonly utilised in photolithography methods for patterning organic or inorganic materials on surfaces, for example, in the fabrication of semi-conductor devices. U.S. Pat. No. 5,744,305 describes the fabrication and use of such masks for photolithography and light-directed spatially-addressable parallel chemical synthesis.

In a further aspect of the invention, photochromic materials may be used to mark discrete patterns of cultured cells for studying time dependent processes which lead to changes in the distribution of a detectable label that are not dependent on migration of cells from one discrete location to another, but which are the result of morphological changes in cells, leading to extension or migration of parts of cells, outwith the areas originally occupied by the cells.

To apply the method of the current invention to neurite outgrowth assays, cultured neuronal cells, for example PC-12 cells (Koike, T., Brain Res., (1983), 289(1-2), 293-303) are labelled with a suitable photochromic marker substance and subsequently exposed to a suitable wavelength of light so as to render the marker substance detectable in a defined pattern over an sub-population of cells. Subsequent re-examining of the specimen at different time intervals by illuminating the cells with light of a wavelength suitable for detection of the marker substance will reveal the presence of absence of neurite outgrowth by detecting the appearance of the detectable label in regions of the specimen not subject to patterned illumination, such appearance being caused by outgrowth of neurites from cell bodies.

EXAMPLES

Example 1

HeLa cells were grown in 12 well multiwell dishes in DMEM+10% serum. Cells were washed in PBS and cell surface proteins labelled with CMNB-caged carboxy-fluorescein succinimidyl ester (Molecular Probes) at 0.025 mg/ml for 1 hour at room temperature. Cells were washed three times with PBS and then exposed to 330-380 nm light from a mercury lamp using a 20× objective on a Nikon Diaphot 300 microscope with the illumination iris closed to the maximum extent. Lateral movement of the microscope stage was used to uncage the carboxy-fluorescein in a line across the cell culture. Subsequent changing of the excitation wavelength to 450-490 nm and opening of the illumination iris revealed a line of marked cells in which the caged label had been converted to a detectable form which were clearly visible as brightly fluorescing cells against a background of endogenous cell fluorescence (FIG. 3).

Example 2

Figure 4:
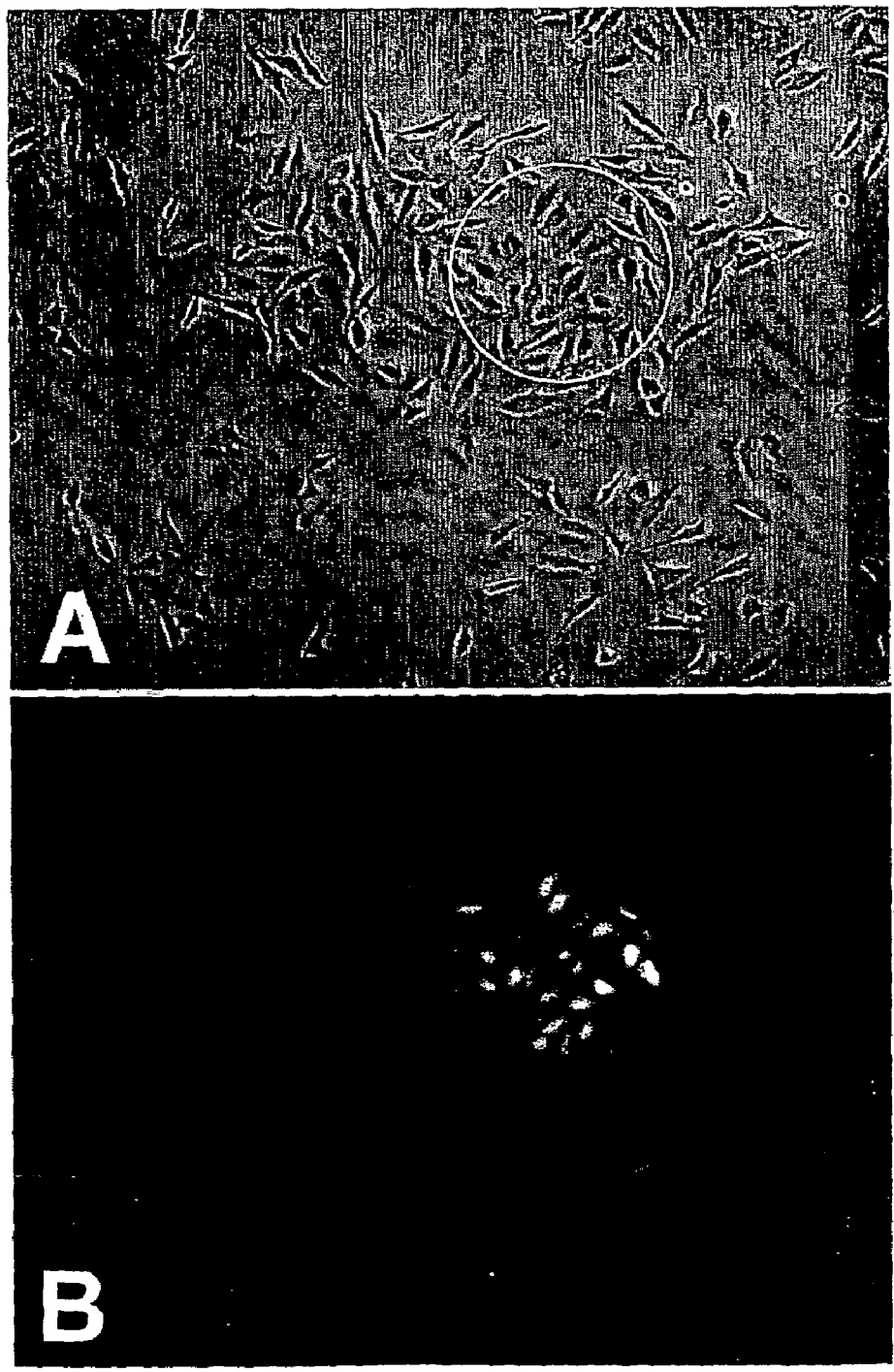
FIGS. 4(A and B) is an electronic image showing HeLa cells loaded with a caged fluor and patterned using UV light.

HeLa cells were grown in 12 well multiwell dishes in DMEM+10% serum. Cells were loaded with 0.1 mg/ml CMNB-caged fluorescein (Molecular Probes) using Influx Pinocytic cell-loading reagent (Molecular Probes) according to the suppliers instructions. Cells were exposed to 330-380 nm light from a mercury lamp using a 10× objective on a Nikon Diaphot 300 microscope with the illumination iris closed to the maximum extent to illuminate a circular area (FIG. 4A circled, phase contrast image). Subsequent changing of the excitation wavelength to 450-490 nm and opening of the illumination iris revealed a group of marked cells in which the caged label had been converted to a detectable form which were clearly visible as brightly fluorescing cells (FIG. 4B, fluorescence image)

Example 3

Figure 5:
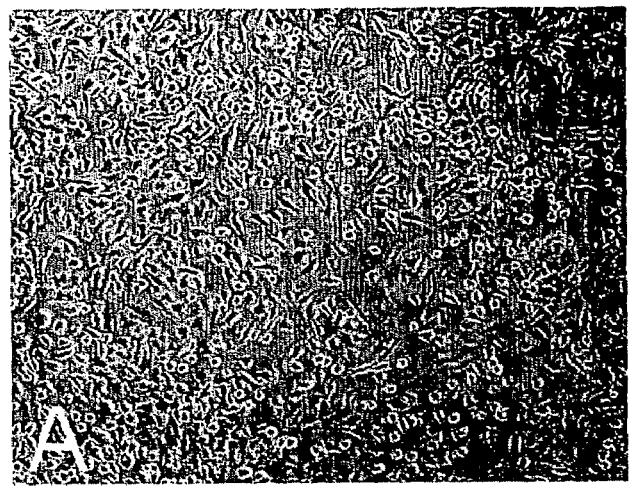
FIGS. 5(A, B and C) shows HeLa cells loaded with a caged fluor and patterned using UV light.
Figure 5:
Figure 5:
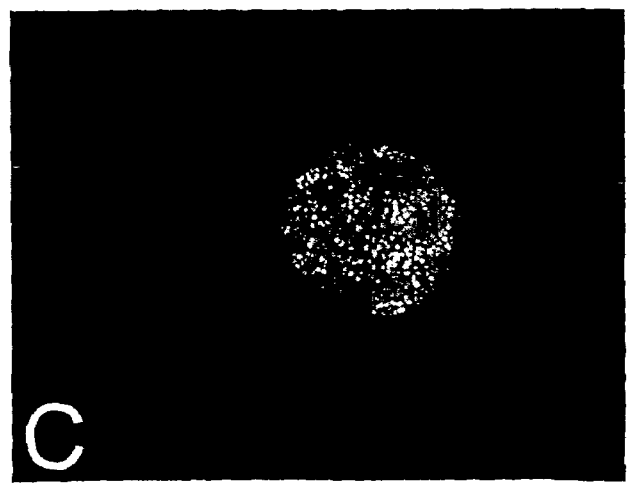

HeLa cells were grown in 24 well plates in DMEM+10% serum. Cells were loaded with 1 mg/ml CMNB-caged fluorescein (Molecular Probes) using Influx Pinocytic cell-loading reagent (Molecular Probes) according to the suppliers instructions and transferred into low fluorescence Hams F-12 media. Cells were exposed to 330-380 nm light from a mercury lamp using a 10× objective on a Nikon Diaphot 300 microscope with the illumination iris partially closed to illuminate a circular area. Subsequent changing of the excitation wavelength to 450-490 nm and opening of the illumination iris revealed a group of marked cells in which the caged label had been converted to a detectable form which were clearly visible as brightly fluorescing cells with a 10× objective (FIG. 5B) and as an island of fluorescing cells at lower magnification using a 4× objective (FIG. 5C) clearly distinguishable from the total population of cells which were only visible by phase contrast examination (FIG. 5A).

Example 4

Figure 6:
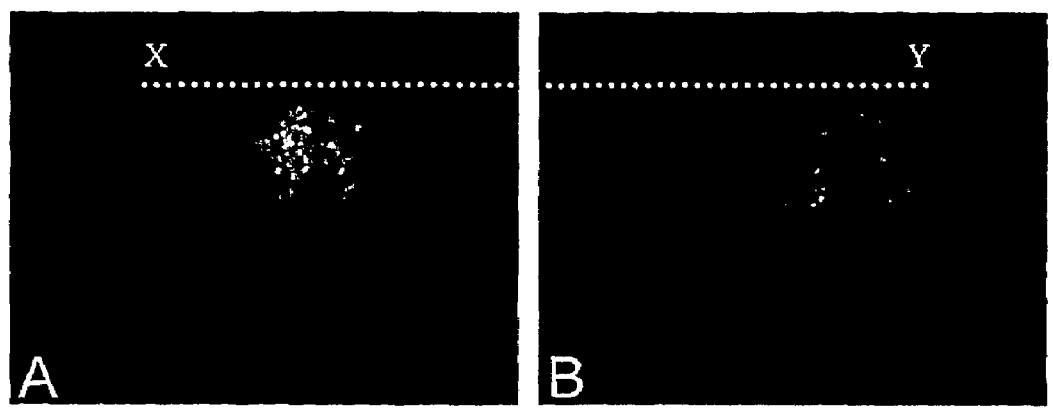
FIGS. 6 (A, B and C) shows HeLa cells loaded with a caged fluor, patterned using UV light and fluorescence distribution analysed at 0 and 24 hours.
Figure 6:
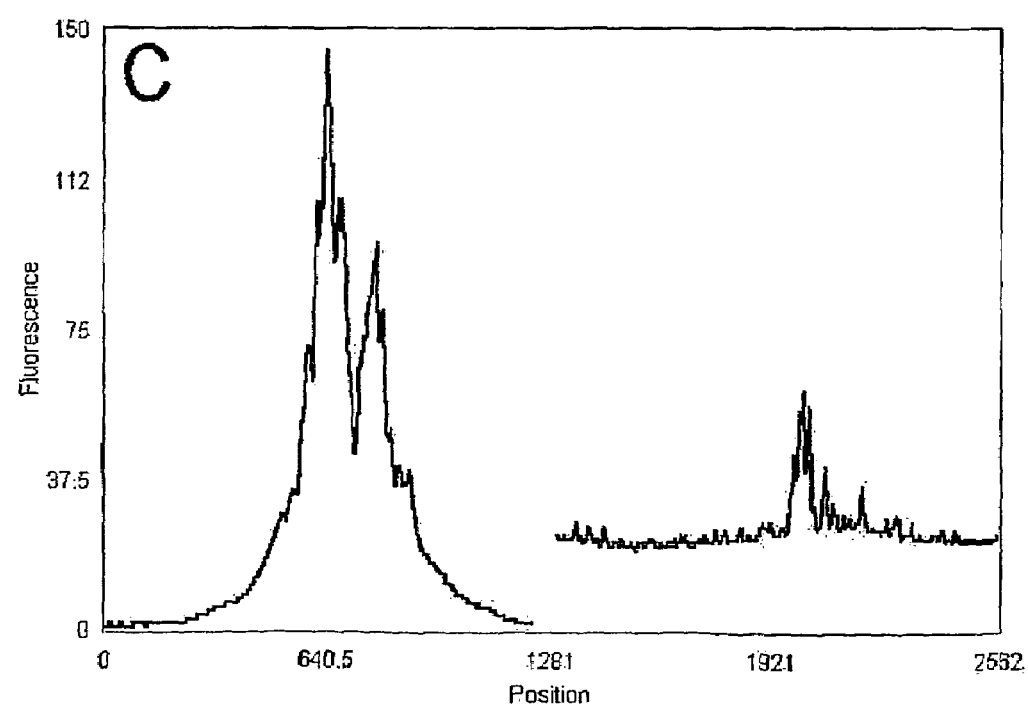

HeLa cells were grown in Wellco glass bottom dishes in Hams F-12+10% serum. Cells were loaded with 1 mg/ml CMNB-caged fluorescein (Molecular Probes) using Influx Pinocytic cell-loading reagent (Molecular Probes) according to the suppliers instructions. Cells were exposed to 330-380 nm light from a mercury lamp using a 20× objective on a Nikon Diaphot 300 microscope with the illumination iris partially closed to illuminate a circular area. One image (FIG. 6A) was recorded immediately and a further image of the same area of the culture dish was acquired after 24 hours incubation at 37° C. (FIG. 6B). Fluorescence intensity across the area was determined along the line X-Y was determined using Metamorph image analysis software (FIG. 6C) which showed a clear decrease in peak intensity and a raised general fluorescence consistent with movement of cells away from the marked area due to random cell migration in the 24 hours separating the images.

What is claimed is:

1. A method of measuring a change in cellular morphology comprising:
    a) exposing a region containing a sub-population of cells in a cell population to an activation light of a first wavelength, wherein said cell population is labelled with a non-fluorescent caged fluorescent molecule, to irreversibly activate said caged fluorescent molecule in the sub-population of cells to an active fluorescent form;
    b) at a first subsequent time exposing at least a portion of said cell population to a fluorescent excitation light of a second and different wavelength and detecting a first pattern of distribution of said fluorescent molecule; and
    c) at a second time exposing said portion of said cell population of step (b) to light of the second wavelength and detecting a second pattern of distribution of said fluorescent molecule;
    wherein a difference between said first and second patterns of distribution of said fluorescent molecule is indicative of a change in said cellular morphology and further wherein said method does not include tracking of individual cells.

2. The method of claim 1, wherein said cellular morphology is selected from the group consisting of cell size and cell shape, or the combination thereof.

3. The method of claim 2, wherein the cellular morphology is cell shape and said change is indicative of neurite outgrowth.

4. The method of claim 1, further comprising following step c): exposing said portion of said cell population to light of said second wavelength N further times where N is ≧1, and detecting a pattern of distribution of said fluorescent molecule wherein the patterns of distribution of said fluorescent molecule are used to create a profile indicative of changes in said cellular morphology.

5. The method of claim 1, wherein said caged fluorescent molecule is selected from the group consisting of N-(DMNB-caged fluorescein)- 1,2-dihexadecanoyl-sn-glycero-3-phosphoethanolamine and 5-carboxyfluorescein-bis-(5- carboxymethoxy-2-nitrobenzyl) ether-alanine-carboxamide, succinimidyl ester.

6. A method of measuring a change in cell position comprising:
    a) exposing a region containing a sub-population of cells in a cell population to an activation light of a first wavelength, wherein said cell population is labelled with a non-fluorescent caged fluorescent molecule, to irreversibly activate said caged fluorescent molecule in the sub-population of cells to an active fluorescent form;
    b) at a first subsequent time exposing at least a portion of said cell population to a fluorescent excitation light of a second and different wavelength and detecting a first pattern of distribution of said fluorescent molecule; and
    c) at a second subsequent time exposing said portion of said cell population of step (b) to light of the second wavelength and detecting a second pattern of distribution of said fluorescent molecule;
    wherein a difference between said first and second patterns of distribution of said fluorescent molecule is indicative of a change in said cell position, and further wherein said method does not include tracking of individual cells.

7. The method of claim 6, further comprising following step c):
    exposing said portion of said cell population to light of said second wavelength N further times where N is ≧1, and detecting a pattern of distribution of said fluorescent molecule wherein the patterns of distribution of said fluorescent molecule are used to create a profile indicative of changes in said cell position.

8. The method of claim 6, wherein said caged fluorescent molecule is selected from the group consisting of N-(DMNB-caged fluorescein)-1,2-dihexadecanoyl-sn-glycero-3-phosphoethanolamine and 5-carboxyfluorescein-bis-(5-carboxymethoxy-2-nitrobenzyl) ether-alanine-carboxamide, succinimidyl ester.

* * * * *